(12) United States Patent
Ree et al.

(10) Patent No.: US 7,285,650 B2
(45) Date of Patent: Oct. 23, 2007

(54) **CLONING AND SEQUENCING OF THE ALLERGEN DAC G5 OF *DACTYLIS GLOMERATA* POLLEN, ITS PREPARATION AND ITS USE**

(75) Inventors: Ronald Van Ree, Amsterdam (NL); Erica Van Oort, Vleuten (NL); Caroline Bonneau, Rouen (FR); Loic Faye, Saint-Jacques-sur-Darnetal (FR); Veronique Gomord, Rouen (FR)

(73) Assignees: Seita Groupe Altadis (FR); Stallergenes (FR)

( * ) Notice: Subject to any disclaimer, the term of this patent is extended or adjusted under 35 U.S.C. 154(b) by 532 days.

(21) Appl. No.: 10/303,426

(22) Filed: Nov. 25, 2002

(65) Prior Publication Data

US 2003/0147880 A1 Aug. 7, 2003

Related U.S. Application Data

(63) Continuation of application No. PCT/FR01/01666, filed on May 29, 2001.

(30) Foreign Application Priority Data

May 29, 2000 (FR) .................................. 00 06857

(51) Int. Cl.
 *C07H 21/04* (2006.01)

(52) U.S. Cl. .................. 536/23.1; 435/325; 435/320.1; 435/252.1; 800/317.3

(58) Field of Classification Search ..................... None
See application file for complete search history.

(56) References Cited

U.S. PATENT DOCUMENTS 5,550,038 A * 8/1996 Goodman et al. ......... 435/70.1

FOREIGN PATENT DOCUMENTS

| WO | WO93/04174 | 3/1993 |
| WO | WO95/06728 | 3/1995 |

OTHER PUBLICATIONS

Campbell, N.A., Biology $2^{nd}$ edition, 1990, The Benjamin/Cummings Publishing Company Inc., pp. 322-347.*
Blumenthal et al., in Allergens and Allergen Immunotherapy, $3^{rd}$ edition, 2004, Marcel Dekker, Inc., pp. 37-50.*
Burks et al., Eur. J. Biochem, 1997, 245:334-339.*
Chapman, M., chapter 3 of Allergens and Allergen Immunotherapy, $3^{rd}$ edition, editors Lockey and Bukantz, Marcel Dekker, Inc. 2004, pp. 51-64.*

* cited by examiner

*Primary Examiner*—G. R. Ewoldt
*Assistant Examiner*—Michael Szperka
(74) *Attorney, Agent, or Firm*—DLA Piper US LLP

(57) ABSTRACT

A purified nucleic acid molecule comprising a nucleotide sequence coding for allergen Dac g5 having amino acid sequence SEQ ID NO. 2, a derivative or a fragment thereof.

13 Claims, 2 Drawing Sheets

Fig.1

| | | | | | | | | | | | | | | | | | |
|---|---|---|---|---|---|---|---|---|---|---|---|---|---|---|---|---|---|
| ATG | GCG | GTC | CAG | AAG | TAC | ACC | GTG | GCT | CTA | TTC | CTC | GCC | GTG | GTC | CTG | GTA | GCG | 54 |
| M | A | V | Q | K | Y | T | V | A | L | F | L | A | V | V | L | V | A | 18 |

| | | | | | | | | | | | | | | | | | |
|---|---|---|---|---|---|---|---|---|---|---|---|---|---|---|---|---|---|
| GGC | CCG | GTC | GCC | TCC | TAC | GCC | GCC | GAC | GCC | GGC | TAC | ACC | CCG | GCC | GCC | GCG | GCC | 108 |
| G | P | V | A | S | Y | A | A | D | A | G | Y | T | P | A | A | A | A | 36 |

| | | | | | | | | | | | | | | | | | |
|---|---|---|---|---|---|---|---|---|---|---|---|---|---|---|---|---|---|
| ACC | CCG | GCT | ACC | GCT | GGA | GGG | AAG | GCG | ATG | ACC | GAG | GAG | CAG | ACG | CTA | ATC | GAG | 162 |
| T | P | A | T | A | G | G | K | A | M | T | E | E | Q | T | L | I | E | 54 |

| | | | | | | | | | | | | | | | | | |
|---|---|---|---|---|---|---|---|---|---|---|---|---|---|---|---|---|---|
| GAC | GTC | AAT | GCT | GGT | TTC | AAG | GCG | GCC | GTG | GCC | GCC | GCC | TCC | AGT | GCC | CCT | CCG | 216 |
| D | V | N | A | G | F | K | A | A | V | A | A | A | S | S | A | P | P | 72 |

| | | | | | | | | | | | | | | | | | |
|---|---|---|---|---|---|---|---|---|---|---|---|---|---|---|---|---|---|
| GCG | GAC | AAG | TTC | AAG | ACC | TTC | GAG | GCC | ACC | TTC | ACT | GCG | GCC | TGC | AAG | GCT | AAC | 270 |
| A | D | K | F | K | T | F | E | A | T | F | T | A | A | C | K | A | N | 90 |

| | | | | | | | | | | | | | | | | | |
|---|---|---|---|---|---|---|---|---|---|---|---|---|---|---|---|---|---|
| ATC | GCC | GCC | GCC | GCC | ACC | AAG | GTG | CCC | CTG | TTC | GTC | GCC | AAG | CTC | GAC | GCC | GCC | 324 |
| I | A | A | A | A | T | K | V | P | L | F | V | A | K | L | D | A | A | 108 |

| | | | | | | | | | | | | | | | | | |
|---|---|---|---|---|---|---|---|---|---|---|---|---|---|---|---|---|---|
| TAC | GCC | GTC | GCC | TAC | AAG | ACC | GCC | ACG | GGC | CCC | ACC | CCC | GAG | GCC | AAG | TAC | GAC | 378 |
| Y | A | V | A | Y | K | T | A | T | G | P | T | P | E | A | K | Y | D | 126 |

| | | | | | | | | | | | | | | | | | |
|---|---|---|---|---|---|---|---|---|---|---|---|---|---|---|---|---|---|
| GCC | TTC | GTC | GCC | GCC | CTC | ACC | GAA | GCG | CTC | CGC | GTT | ATC | GCC | GGC | GCC | CTC | GAA | 432 |
| A | F | V | A | A | L | T | E | A | L | R | V | I | A | G | A | L | E | 144 |

| | | | | | | | | | | | | | | | | | |
|---|---|---|---|---|---|---|---|---|---|---|---|---|---|---|---|---|---|
| GTC | CAT | GCC | GTC | AAG | CCC | GCT | GCC | GAG | GAG | GTT | CCC | GCG | GCC | AAG | ATC | CCC | GCC | 486 |
| V | H | A | V | K | P | A | A | E | E | V | P | A | A | K | I | P | A | 162 |

| | | | | | | | | | | | | | | | | | |
|---|---|---|---|---|---|---|---|---|---|---|---|---|---|---|---|---|---|
| GGT | GAG | CTG | CAG | ATT | GTC | GAC | AAG | ATC | GAC | GCC | GCC | TAC | AAG | ATC | GCA | GCC | ACC | 540 |
| G | E | L | Q | I | V | D | K | I | D | A | A | Y | K | I | A | A | T | 180 |

| | | | | | | | | | | | | | | | | | |
|---|---|---|---|---|---|---|---|---|---|---|---|---|---|---|---|---|---|
| GCT | GCA | AAC | GCC | GCC | CCC | GCC | AAC | GAC | AAG | TTC | ACC | GTC | TTC | GAG | GGC | GCC | TTC | 594 |
| A | A | N | A | A | P | A | N | D | K | F | T | V | F | E | G | A | F | 198 |

| | | | | | | | | | | | | | | | | | |
|---|---|---|---|---|---|---|---|---|---|---|---|---|---|---|---|---|---|
| AAC | AAG | GCC | ATC | AAG | GAG | AGC | ACC | GGC | GGC | GCA | TAC | GAG | AGT | TAC | AAG | TTC | ATC | 648 |
| N | K | A | I | K | E | S | T | G | G | A | Y | E | S | Y | K | F | I | 216 |

| | | | | | | | | | | | | | | | | | |
|---|---|---|---|---|---|---|---|---|---|---|---|---|---|---|---|---|---|
| CCC | ACG | CTT | GAG | GCC | GCG | GTC | AAG | CAG | GCT | TAC | GCC | GCC | ACC | GTG | GCC | GCC | GCG | 702 |
| P | T | L | E | A | A | V | K | Q | A | Y | A | A | T | V | A | A | A | 234 |

| | | | | | | | | | | | | | | | | | |
|---|---|---|---|---|---|---|---|---|---|---|---|---|---|---|---|---|---|
| CCG | GAG | GTC | AAG | TAC | GCC | GTC | TTT | GAG | GCC | GCG | CTG | ACC | AAG | GCC | ATC | ACC | GCC | 756 |
| P | E | V | K | Y | A | V | F | E | A | A | L | T | K | A | I | T | A | 252 |

| | | | | | | | | | | | | | | | | | |
|---|---|---|---|---|---|---|---|---|---|---|---|---|---|---|---|---|---|
| ATG | TCC | GAG | GCA | GAG | AAG | GTC | GCC | ACG | CCT | GCC | GCC | GTT | GCT | ACA | GGT | GCG | GCA | 810 |
| M | S | E | A | Q | K | V | A | T | P | A | A | V | A | T | G | A | A | 270 |

| | | | | | | | | | | | | | | | | | |
|---|---|---|---|---|---|---|---|---|---|---|---|---|---|---|---|---|---|
| ACC | GCC | GCT | GCC | AGT | GCT | GCT | ACC | GGC | GCT | GCC | ACC | GCC | GCT | GCC | GGT | GGC | TAC | 864 |
| T | A | A | A | S | A | A | T | G | A | A | T | A | A | A | G | G | Y | 288 |

| | | |
|---|---|---|
| AAA | GTC | TGA | 873 |
| K | V | * | |

Primer F1: ggg tct aga atc ccg gtc cag aag tac acc
Primer F2: aag ctc gag aaa aga gcc gac gcc ggc tac acc
Primer R1: ggg gag ctc tca gac ttt gta gcc acc ggc
Primer R2: ggg ggc ggc cgc tca gac ttt gta gcc acc ggc

B

```
         ────────F1─────────────▶
ATG GCG GTC CAG AAG TAC ACC GTG GCT CTA TTC CTC GCC GTG GTC CTG GTA GCG    54
 M   A   V   Q   K   Y   T   V   A   L   F   L   A   V   V   L   V   A    18
                                 ─────F2──────▶
GGC CCG GTC GCC TCC TAC GCC GCC GAC GCC GGC TAC ACC CCG GCC GCC GCG GCC   108
 G   P   V   A   S   Y   A   A   D   A   G   Y   T   P   A   A   A   A    36

ACC CCG GCT ACC GCT GGA GGG AAG GCG ATG ACC GAG GAG CAG ACG CTA ATC GAG   162
 T   P   A   T   A   G   G   K   A   M   T   E   E   Q   T   L   I   E    54

GAC GTC AAT GCT GGT TTC AAG GCG GCC GTG GCC GCC GCC TCC AGT GCC CCT CCG   216
 D   V   N   A   G   F   K   A   A   V   A   A   A   S   S   A   P   P    72

GCG GAC AAG TTC AAG ACC TTC GAG GCC ACC TTC ACT GCG GCC TGC AAG GCT AAC   270
 A   D   K   F   K   T   F   E   A   T   F   T   A   A   C   K   A   N    90

ATC GCC GCC GCC GCC ACC AAG GTG CCC CTG TTC GTC GCC AAG CTC GAC GCC GCC   324
 I   A   A   A   A   T   K   V   P   L   F   V   A   K   L   D   A   A   108

TAC GCC GTC GCC TAC AAG ACC GCC ACG GGC CCC ACC CCC GAG GCC AAG TAC GAC   378
 Y   A   V   A   Y   K   T   A   T   G   P   T   P   E   A   K   Y   D   126

GCC TTC GTC GCC GCC CTC ACC GAA GCG CTC CGC GTT ATC GCC GGC GCC CTC GAA   432
 A   F   V   A   A   L   T   E   A   L   R   V   I   A   G   A   L   E   144

GTC CAT GCC GTC AAG CCC GCT GCC GAG GAG GTT CCC GCG GCC AAG ATC CCC GCC   486
 V   H   A   V   K   P   A   A   E   E   V   P   A   A   K   I   P   A   162

GGT GAG CTG CAG ATT GTC GAC AAG ATC GAC GCC GCC TAC AAG ATC GCA GCC ACC   540
 G   E   L   Q   I   V   D   K   I   D   A   A   Y   K   I   A   A   T   180

GCT GCA AAC GCC GCC CCC GCC AAC GAC AAG TTC ACC GTC TTC GAG GGC GCC TTC   594
 A   A   N   A   A   P   A   N   D   K   F   T   V   F   E   G   A   F   198

AAC AAG GCC ATC AAG GAG AGC ACC GGC GGC GCA TAC GAG AGT TAC AAG TTC ATC   648
 N   K   A   I   K   E   S   T   G   G   A   Y   E   S   Y   K   F   I   216

CCC ACG CTT GAG GCC GCG GTC AAG CAG GCT TAC GCC GCC ACC GTG GCC GCC GCG   702
 P   T   L   E   A   A   V   K   Q   A   Y   A   A   T   V   A   A   A   234

CCG GAG GTC AAG TAC GCC GTC TTT GAG GCC GCG CTG ACC AAG GCC ATC ACC GCC   756
 P   E   V   K   Y   A   V   F   E   A   A   L   T   K   A   I   T   A   252

ATG TCC GAG GCA CAG AAG GTC GCC ACG CCT GCC GCC GTT GCT ACA GGT GCG GCA   810
 M   S   E   A   Q   K   V   A   T   P   A   A   V   A   T   G   A   A   270

ACC GCC GCT GCC AGT GCT GCT ACC GGC GCT GCC ACC GCC GCT GCC GGT GGC TAC   864
 T   A   A   A   S   A   A   T   G   A   A   T   A   A   A   G   G   Y   288
                                                  ◀─────────────────────

AAA GTC TGA                                                                873
 K   V   *
```

R1 and R2

CLONING AND SEQUENCING OF THE ALLERGEN DAC G5 OF *DACTYLIS GLOMERATA* POLLEN, ITS PREPARATION AND ITS USE

RELATED APPLICATION

This is a continuation of International Application No. PCT/FR01/01666, with an international filing date of May 29, 2001, which is based on French Patent Application No. 00/06857, filed May 29, 2000.

FIELD OF THE INVENTION

This invention relates to the cloning and sequencing of *Dactylis glomerata* pollen allergens, more particularly, the allergen Dac g 5. The invention also relates to the production of the recombinant allergen for incorporation in preparations useful for the diagnosis or treatment of allergies.

BACKGROUND

Allergens are the most abundant proteins of pollen and constitute the major cause of allergies in temperate regions.

Certain genetically predisposed individuals become hypersensitive (allergic) to antigens stemming from extremely varied environmental sources. Antigens capable of inducing an immediate or delayed hypersensitization reaction are referred to as allergens. Allergens can have as their origin notably trees, herbaceous plants, insects, mammals, food, drugs and chemical products. Allergens are classified in groups I to V according to their immunochemical properties. The allergen Dac g 5 of *Dactylis glomerata* belongs to group V as does the allergen Lol p V of *Lolium perenne*.

The antibodies involved in allergy belong to the IgE class of immunoglobulins. In the presence of an allergen, IgE binds to mastocytes and basophils, which leads to the release by these cells of different chemical mediators and thus to the manifestation of allergy. Allergy can be manifested in different forms such as, e.g., anaphylactic shock, asthma, rhinitis or atopic dermatitis.

When the diagnosis of allergy to a particular compound has been established, desensitization of the patient in relation to the implicated allergen is the most frequent therapeutic approach, especially when the presence of the allergen cannot be avoided as in the case of pollen and acarids. This type of treatment has proven to be effective, but it requires the availability of an effective and safe product. In fact, the treatment presents a risk of anaphylactic shock such that the administered product must be free of any impurities that could constitute another potential allergen. At present, it is only known to use complex mixtures of allergens and not pure products. It is, therefore, necessary to have available allergens in a structural form as close as possible to the natural allergen and having the highest possible degree of purity.

One of the possible means for attaining this goal is the production of recombinant allergens in a host organism (Laffer, S. et al., J. Allergy Clin. Immunol., September 1996, volume 98, no. 3, pages 652-658).

As examples, we can cite the patent application published as No. 819 763 which describes the production of the modified allergen Der f II. The European patent published as No. 406 286 describes the cloning of a major allergen of rye grass pollen, Lol p 1, and the expression of this gene. The patent application published as No. 473 111 also discloses the production of recombinant acarid allergens used for desensitization. The patent application published as No. 463 059 pertains to allergens taken from ragweed and the use of these proteins. These applications disclose the expression of genes and the production of proteins in *E. coli*.

This system of expression has the disadvantage of not enabling the post-translational modifications of the proteins which can be implemented in eukaryote cells. For example, the proteins produced are not glycosylated. However, the glycosylation of certain allergen proteins can be important for their ability to bind to IgE (Van Ree et al., J. Biol. Chem., 2000, volume 275, pages 11451-11458).

SUMMARY OF THE INVENTION

This invention relates to a purified nucleic acid molecule including a nucleotide sequence coding for allergen Dac g 5 having amino acid sequence SEQ ID NO.2, a derivative or a fragment thereof.

This invention also relates to a process for producing recombinant protein Dac g 5, an isoform, a fragment or a functional or immunologic equivalent thereof, including culturing a prokaryote or eukaryote organism transformed by a nucleic acid molecule under conditions and for a sufficient length of time to enable expression of the protein, and isolating proteins produced from the transformed organisms.

This invention further relates to a pharmaceutical composition for treating or diagnosing an allergy, including a therapeutically effective amount of a protein or an antibody directed against the protein.

This invention still further relates to a process for detecting sensitivity manifested by an individual to pollen of *Dactylis glomerata*, including contacting a sample obtained from an individual with a protein or an antibody directed against the protein under conditions enabling formation of an antigen/antibody complex, and detecting presence of the complex.

BRIEF DESCRIPTION OF THE DRAWINGS

FIG. 1 is an amino acid sequence of the proform of the allergen Dac g 5.

FIG. 2A is the amino acid sequence of the proform of the sense primer.

FIG. 2B is the amino acid sequence of the proform of the allergen Dac g 5 and the positioning of the primers on the sequence.

DETAILED DESCRIPTION

This invention pertains to the cloning, sequencing and preparation of a purified nucleic acid molecule comprising a nucleotide sequence coding for the protein constituting the allergen Dac g 5 or for a derivative thereof. The invention also pertains to insertion of this nucleic acid into an expression vector and production of the recombinant protein in a host organism or microorganism, in plant cells and plants or parts of plants, and preferably in tobacco plant cell suspensions and tobacco plants. This allergen is produced for the purpose of using it in diagnostics and immunotherapy.

The production of allergens in plant cells such as, e.g., tobacco plant cells, has the advantage of enabling production of glycosylated recombinant proteins. This production means has not been used to date for the production of allergens.

The studies performed in the framework of this invention concerned:

cloning the cDNA of Dac g 5, insertion of the cloned nucleic acid molecule in a suitable expression vector, production of recombinant Dac g 5 in biological systems, immunologic tests of the purified allergen.

Dac g 5 is a 26.5-kDa protein of 265 amino acids recognized by at least about 90% of subjects allergic to grass pollens.

Allergen Dac g 5 of *Dactylis glomerata* belongs to the group V allergens. Nucleotide sequences coding for allergens homologous to Dac g 5 have been described in the prior art. The inventors defined degenerated oligonucleotides from these sequences to specifically amplify using the RT-PCR technique a cDNA coding Dac g 5. A cDNA fragment of expected size was cloned from a total RNA population of *Dactylis glomerata* and then sequenced. This fragment was used to define specific primers for the RACE-PCR 5' and 3' protocols. These protocols enabled completion of the 5' and 3' ends of the fragment. The complete cDNA coding for Dac g 5 was sequenced after amplification of the 5' and 3' ends.

The sequences obtained enabled definition of new specific primers of Dac g 5. These primers were used to clone the cDNA of the proform and mature form of the allergen. The nucleotide sequences of the primers used for the PCR reactions were the following:

sense primer (proform), represented in FIG. 2A (primer C1) and as SEQ ID NO. 9 in the attached sequence listing:

5'GGG TCT AGA ATG GCG GTC CAG AAG TAC ACC 3' antisense primer used for cloning the proform, represented in FIG. 2A (primer F1) and as SEQ ID NO. 10 in the attached sequence listing:

5'GGG GAG CTC TCA GAC TTT GTA GCC ACC GGC 3' sense primer (mature form), represented in FIG. 2A (primer F2) and as SEQ ID NO. 11 in the attached sequence listing:

5'AAG CTC GAG AAA AGA GCC GAC GCC GGC TAC ACC 3' antisense primer used for cloning the mature form, represented in FIG. 2A (primer R2) and as SEQ ID NO. 12 in the attached sequence listing:

5'GGG GGC GGC CGC TCA GAC TTT GTA GCC ACC GGC 3'

The cDNA clones were sequenced and the amino acid sequence corresponding to each nucleotide sequence was determined.

The inventors were, thus, able to clone and sequence the nucleic acid coding for the allergen Dac g 5 of *Dactylis glomerata* pollen. The invention consequently pertains to a purified nucleic acid molecule constituted by or comprising a nucleotide sequence coding for the allergen Dac g 5, a derivative or a fragment thereof. The amino acid sequence of the proform of the allergen Dac g 5 is represented in FIG. 1 and as SEQ ID NO. 2 in the attached sequence listing. A fragment of this sequence delimited by the amino acids in positions 25 to 290 constitutes the mature Dac g 5 protein. The amino acid sequence of the mature form of the allergen Dac g 5 is represented in FIG. 1 and as SEQ ID NO. 4 in the attached sequence listing.

FIG. 1 gives the nucleotide and peptide sequence of the proform of the allergen Dac g 5 (isoform 1). The underlined sequence corresponds to the absent signal sequence of the mature protein. The codons and amino acids which are different in isoform 2 are in boxes. Table 1 below indicates the variations observed between isoforms 1 and 2.

TABLE 1

| Amino acid position | Isoform 1 | Isoform 2 |
|---|---|---|
| 40 | Thr (ACC) | Ala (GCT) |
| 51 | Thr (ACG) | Lys (AAG) |
| 265 | Val (GTT) | Ala (GCT) |

FIG. 2A represents the sequences of the primers (SEQ ID NOS 9, 11, 10, and 12, respectively, in order of appearance) and FIG. 2B (SEQ ID NOS 1-2) the sequence of the proform of the allergen Dac g 5 and the positioning of the primers on this sequence.

The term "derivative of the protein constituting the allergen Dac g 5" is understood to mean a protein whose amino sequence differs by the modification, suppression or addition of one or more amino acids, but is functionally and/or immunologically equivalent to Dac g 5.

Such modifications can result from the degeneration of the genetic code or modifications of the nucleotide acid sequence by any molecular biology technique. The expert in the field is able to determine among these sequences those which have functional and immunological properties identical or substantially identical to or close to those of Dac g 5, e.g., by means of an antibody. In this context, the inventors cloned two isoforms of Dac g 5. The amino acid sequences of these mature isoforms of the allergen Dac g 5 are represented as SEQ ID NO. 6 and SEQ ID NO. 8 in the attached sequence listing.

The invention thus also envisages the isoforms of the protein constituting the allergen Dac g 5 and has a homology of amino acid sequences greater than about 50%, preferably greater than about 70% and especially preferably greater than about 90% with the sequence represented as SEQ ID NO. 2 in the attachment. The invention envisages, more particularly, a protein, functional derivative and immunologically equivalent to Dac g 5 whose amino acid sequence is selected from among the sequences SEQ ID NO. 6 and SEQ ID NO. 8 in the attached sequence listing.

The term "fragment of the protein constituting the allergen Dac g 5" is understood to mean any peptide or polypeptide stemming from the protein, more particularly useful for the diagnosis of allergy.

A purified nucleic acid molecule comprising or constituted by a nucleotide sequence (cDNA) coding for the proform of the allergen Dac g 5 is represented as SEQ ID NO. 1 in the attached sequence listing. The invention also pertains to a derivative or fragment thereof and, more particularly, a nucleic acid molecule coding for the mature protein which is delimited by the nucleotides in positions 75 to 870 of the nucleotide sequence represented as SEQ ID NO. 1 in the attached sequence listing. This sequence is represented as SEQ ID NO. 3 in the attached sequence listing.

The invention also pertains to the nucleic acid molecules coding the isoforms of the mature Dac g 5 protein and, more particularly, those whose amino acid sequences are represented as SEQ ID NO. 6 and SEQ ID NO. 8 in the attached sequence listing.

On the basis of the nucleotide sequences coding for Dac g 5 or one of its isoforms, the expert in the field can define nucleotide sequences coding for proteins or polypeptides corresponding to a fragment of Dac g 5 or one of its isoforms and possessing, e.g., at least one epitope of Dac g 5 or one epitope of one of the isoforms of Dac g 5. The expert in the field can also define a nucleotide sequence coding for proteins functionally equivalent to Dac g 5 or to one of its isoforms but whose amino acid sequence is not identical to that of Dac g 5 or to that of one of its isoforms.

Finally, the expert in the field can define a nucleotide sequence coding for proteins immunologically equivalent to Dac g 5 or to one of its isoforms. These proteins are, e.g., capable of binding to the anti-Dac g 5 antibodies, but do not possess the enzymatic function of the natural Dac g 5 allergen. The phrase "derivative of a nucleic acid according to the invention" is understood more particularly to mean a nucleic acid molecule capable of hybridizing under standard hybridization conditions with one of the sequences represented as SEQ ID NO. 1 and SEQ ID NO. 3 in the attached sequence listing. These comprise, for example, the nucleotide sequences coding the isoforms of Dac g 5 represented as SEQ ID NO. 5 and SEQ ID NO. 7 in the attached sequence listing.

The invention also includes the mutagenesis of the protein enabling introduction at certain defined positions of the protein one or more sites carrying a particular functional group. Thus, one can introduce, e.g., an N-glycosylation site on the allergen.

The invention also pertains to a recombinant nucleic acid molecule comprising a polynucleotide sequence coding for the allergen Dac g 5 or one of its isoforms or a derivative thereof such as a fragment or a functional and/or immunologic equivalent of the protein Dac g 5 or one of its isoforms, a promoter bound in a functional manner to the sequence, possibly a selection gene placed under the control of its own promoter or of the same promoter as the sequence, and advantageously a termination sequence placed downstream of the sequence. It can be a cassette or preferably an expression vector comprising notably an origin of eukaryote or prokaryote replication, an adapted promoting sequence, a selection marker and a nucleotide sequence coding for the allergen Dac g 5 or one of its isoforms, or a derivative thereof placed under the control of said regulation sequences. The expert in the field can select without difficulty, from among the expression vectors known in the prior art the vector the best adapted to the host organism in which the protein is produced.

The invention envisages most particularly for the production of the protein constituting the allergen Dac g 5 or one of its isoforms a vector enabling expression of the nucleic acid in eukaryote cells, and preferably in plant cells or yeasts.

The expression vector can also be constructed in a manner to enable production of the previously defined recombinant protein in the form of a fusion protein. The polypeptide fused to the protein of interest can notably be useful to enable or facilitate its purification. This polypeptide can in particular be a sequence constituted of multiple histidines or histidine-tags added in a variable region not critical for the activity and conformation of the molecule, such as an internal region or a N-terminal or C-terminal end. The addition of a histidine-tag sequence enables purification of the recombinant protein by affinity chromatography on a chelated metal column.

The invention also pertains to an eukaryote or prokaryote host transformed by an expression vector as described above. This host can be, e.g., *E. coli, Saccharomyces cerevisiae, Pichia pastoris* or a plant cell, notably a *Nicotiana tabacum* cell in the genome of which is incorporated in a stable manner the nucleic acid molecule coding for the allergen Dac g 5 or one of its isoforms or a derivative thereof.

The invention also pertains to an organism or microorganism, preferably a cell or a plant, more preferably a tobacco plant cell which has incorporated in its genome, advantageously in a stable manner, a nucleic acid molecule of the invention placed under regulation sequence control in a manner to express the allergen Dac g 5 or one of its isoforms in these cells, in a plant or a determined part of the plant.

Transgenic plants according to the invention can be prepared by transforming a plant cell with the nucleic acid molecule then regenerating a plant from the transformed cell.

The invention pertains to a process for producing recombinant Dac g 5 protein or one of its isoforms, or a polypeptide fragment of Dac g 5 or one of its isoforms, or a functional or immunologic equivalent of Dac g 5 or one of its isoforms. This process comprises the culture of a prokaryote or eukaryote organism transformed by an expression vector as previously defined under conditions and over a sufficient length of time to enable expression of the protein.

This process also comprises isolation of the produced proteins from the culture of transformed organisms. In the particular case of the expression of recombinant proteins in tobacco plant cells, the cells expressing the allergen of interest are selected by immunodetection using an antibody directed against the natural form of Dac g 5. The allergens are localized by cell fractionation. Then they are purified from transgenic cell suspensions by immunodetection with an antibody directed against the natural form of Dac g 5. The process according to the invention also comprises the structural and immunologic analysis of the protein(s) produced.

The invention, thus, also pertains to the recombinant allergen Dac g 5 or a derivative thereof obtained by the process. The invention pertains to the proform and the mature form of the allergen Dac g 5. The invention also pertains to the isoforms of the mature form of Dac g 5. It also pertains to peptide or polypeptide fragments of Dac g 5 or of one of its isoforms, as well as proteins that are functionally or immunologically equivalent to Dac g 5 or to one of its isoforms. The proteins equivalent to Dac g 5 or to one of its isoforms can be obtained notably by directed mutagenesis applied to the DNA molecule coding for Dac g 5 or for one of its isoforms. The invention also pertains to a recombinant fusion protein comprising the protein Dac g 5 or one of its isoforms, a fragment of these proteins or a functional or immunologic equivalent.

This recombinant allergen, a derivative thereof, like the natural allergen, can be used for preparing monoclonal or polyclonal antibodies. The monoclonal antibodies are prepared according to the conventional techniques with which the expert in the field is quite familiar. The polyclonal antibodies can be obtained by immunizing animals with the allergen Dac g 5 by means of a suitable adjuvant; the antibodies are then purified from the serum of the immunized animals.

These antibodies can notably be employed to detect the presence of the allergen Dac g 5, a peptide fragment of the protein or one of its isoforms or an immunologic equivalent thereof, in a particular medium such as, e.g., a culture medium.

The invention furthermore pertains to pharmaceutical compositions intended for the treatment and/or diagnosis of an allergy and comprising as active principle an effective quantity of Dac g 5, a fragment of one of the isoforms of the protein or a functional or immunologic equivalent thereof, or an antibody directed against them. In these compositions, the active principle is combined with a pharmaceutically acceptable vehicle. The compositions intended for the treatment of allergy are formulated according to suitable principles known by the expert in the field such that it can be injected via the subcutaneous route or administered by any other route.

The invention also pertains to a process for the detection of sensitivity manifested by an individual to herbaceous pollen and, in particular, to the pollen of *Dactylis glomerata*. This process comprises the detection of the presence of antibodies binding to one of the isoforms of the recombinant Dac g 5 protein, a fragment or a functional and/or immunologic equivalent thereof, or a specific antibody of them. This process comprises notably a step during which a sample obtained from the individual is brought into contact with one of the isoforms of the recombinant Dac g 5 protein, a derivative of them or an antibody directed against them, under conditions enabling formation of an antigen/antibody complex, and then the detection of said complex.

The invention finally pertains to a reagent for diagnosis of an allergy characterized in that it comprises a preparation containing one of the isoforms of the recombinant protein Dac g 5 and/or a fragment and/or a derivative of one of the isoforms of Dac g 5, or an antibody directed against them.

The invention claimed is:

1. A purified nucleic acid molecule comprising a nucleotide sequence coding for allergen Dac g 5 comprising the amino acid sequence selected from the group consisting of SEQ ID NO. 2, SEQ ID NO. 4, SEQ ID NO. 6, and SEQ ID NO. 8.

2. The purified nucleic acid molecule according to claim 1, comprising the nucleotide sequence coding for an allergen Dac g 5 comprising amino acid sequence SEQ ID NO. 2.

3. The purified nucleic acid molecule according to claim 1, comprising the nucleotide sequence selected from the group consisting of SEQ ID NO. 1, SEQ ID NO. 3, SEQ ID NO. 5 and SEQ ID NO. 7.

4. The purified nucleic acid molecule according to claim 2, comprising the nucleotide sequence SEQ ID NO. 1.

5. A recombinant nucleic acid molecule comprising the nucleic acid molecule according to any one of claims 1 to 4, a promoter bound to said nucleic acid molecule, a selection gene placed under control of a promoter, and a termination sequence downstream of said nucleic acid molecule.

6. An expression vector comprising an origin of eukaryote or prokaryote replication, and the recombinant nucleic acid molecule according to claim 5.

7. An isolated eukaryote or prokaryote host transformed by the nucleic acid molecule according to claim 5.

8. A eukaryote or prokaryote host transformed by an expression vector according to claim 6.

9. A tobacco plant having incorporated in its genome the nucleic acid molecule according to any one of claims 1 to 4, placed under regulation sequence control in a manner to express allergen Dac g 5 in a selected part of the plant.

10. A tobacco plant cell suspension, whose cells have incorporated in their genome the nucleic acid molecule according to any one of claims 1 to 4, placed under regulation sequence control in a manner to express allergen Dac g 5 in said cells.

11. A yeast having incorporated in its genome the nucleic acid molecule according to any one of claims 1 to 4, placed under regulation sequence control in a manner to express allergen Dac g 5.

12. A process for producing recombinant allergen Dac g 5 comprising:
   culturing a prokaryote or eukaryote organism transformed by the nucleic acid molecule according to claim 5 under conditions and for a sufficient length of time to enable expression of said allergen, and
   isolating allergens produced from the transformed organisms.

13. A process for producing recombinant allergen Dac g 5 comprising:
   culturing a prokaryote or eukaryote organism transformed by the expression vector according to claim 6 under conditions and for a sufficient length of time to enable expression of said allergen, and
   isolating allergens produced from the transformed organisms.

* * * * *

SEQUENCE LISTING

```
<160> NUMBER OF SEQ ID NOS: 12

<210> SEQ ID NO 1
<211> LENGTH: 873
<212> TYPE: DNA
<213> ORGANISM: Dactylis glomerata
<220> FEATURE:
<221> NAME/KEY: CDS
<222> LOCATION: (1)..(870)
<223> OTHER INFORMATION: Dac g5 proform sequence

<400> SEQUENCE: 1 atg gcg gtc cag aag tac acc gtg gct cta ttc ctc gcc gtg gtc ctg      48
Met Ala Val Gln Lys Tyr Thr Val Ala Leu Phe Leu Ala Val Val Leu
  1               5                  10                  15 gta gcg ggc ccg gtc gcc tcc tac gcc gcc gac gcc ggc tac acc ccg      96
Val Ala Gly Pro Val Ala Ser Tyr Ala Ala Asp Ala Gly Tyr Thr Pro
             20                  25                  30 gcc gcc gcg gcc acc ccg gct acc gct gga ggg aag gcg atg acc gag     144
Ala Ala Ala Ala Thr Pro Ala Thr Ala Gly Gly Lys Ala Met Thr Glu
         35                  40                  45 gag cag acg cta atc gag gac gtc aat gct ggt ttc aag gcg gcc gtg     192
Glu Gln Thr Leu Ile Glu Asp Val Asn Ala Gly Phe Lys Ala Ala Val
     50                  55                  60 gcc gcc gcc tcc agt gcc cct ccg gcg gac aag ttc aag acc ttc gag     240
Ala Ala Ala Ser Ser Ala Pro Pro Ala Asp Lys Phe Lys Thr Phe Glu
 65                  70                  75                  80 gcc acc ttc act gcg gcc tgc aag gct aac atc gcc gcc gcc gcc acc     288
Ala Thr Phe Thr Ala Ala Cys Lys Ala Asn Ile Ala Ala Ala Ala Thr
                 85                  90                  95 aag gtg ccc ctg ttc gtc gcc aag ctc gac gcc gcc tac gcc gtc gcc     336
Lys Val Pro Leu Phe Val Ala Lys Leu Asp Ala Ala Tyr Ala Val Ala
            100                 105                 110 tac aag acc gcc acg ggc ccc acc ccc gag gcc aag tac gac gcc ttc     384
Tyr Lys Thr Ala Thr Gly Pro Thr Pro Glu Ala Lys Tyr Asp Ala Phe
        115                 120                 125 gtc gcc gcc ctc acc gaa gcg ctc cgc gtt atc gcc ggc gcc ctc gaa     432
Val Ala Ala Leu Thr Glu Ala Leu Arg Val Ile Ala Gly Ala Leu Glu
    130                 135                 140 gtc cat gcc gtc aag ccc gct gcc gag gag gtt ccc gcg gcc aag atc     480
Val His Ala Val Lys Pro Ala Ala Glu Glu Val Pro Ala Ala Lys Ile
145                 150                 155                 160 ccc gcc ggt gag ctg cag att gtc gac aag atc gac gcc gcc tac aag     528
Pro Ala Gly Glu Leu Gln Ile Val Asp Lys Ile Asp Ala Ala Tyr Lys
                165                 170                 175 atc gca gcc acc gct gca aac gcc gcc ccc gcc aac gac aag ttc acc     576
Ile Ala Ala Thr Ala Ala Asn Ala Ala Pro Ala Asn Asp Lys Phe Thr
```

-continued

```
                       180                 185                 190
gtc ttc gag ggc gcc ttc aac aag gcc atc aag gag agc acc ggc ggc    624
Val Phe Glu Gly Ala Phe Asn Lys Ala Ile Lys Glu Ser Thr Gly Gly
        195                 200                 205 gca tac gag agt tac aag ttc atc ccc acg ctt gag gcc gcg gtc aag    672
Ala Tyr Glu Ser Tyr Lys Phe Ile Pro Thr Leu Glu Ala Ala Val Lys
    210                 215                 220 cag gct tac gcc gcc acc gtg gcc gcc gcg ccg gag gtc aag tac gcc    720
Gln Ala Tyr Ala Ala Thr Val Ala Ala Ala Pro Glu Val Lys Tyr Ala
225                 230                 235                 240 gtc ttt gag gcc gcg ctg acc aag gcc atc acc gcc atg tcc gag gca    768
Val Phe Glu Ala Ala Leu Thr Lys Ala Ile Thr Ala Met Ser Glu Ala
                245                 250                 255 cag aag gtc gcc acg cct gcc gcc gtt gct aca ggt gcg gca acc gcc    816
Gln Lys Val Ala Thr Pro Ala Ala Val Ala Thr Gly Ala Ala Thr Ala
            260                 265                 270 gct gcc agt gct gct acc ggc gct gcc acc gcc gct gcc ggt ggc tac    864
Ala Ala Ser Ala Ala Thr Gly Ala Ala Thr Ala Ala Ala Gly Gly Tyr
        275                 280                 285 aaa gtc tga                                                        873
Lys Val
    290

<210> SEQ ID NO 2
<211> LENGTH: 290
<212> TYPE: PRT
<213> ORGANISM: Dactylis glomerata

<400> SEQUENCE: 2

Met Ala Val Gln Lys Tyr Thr Val Ala Leu Phe Leu Ala Val Val Leu
1               5                   10                  15

Val Ala Gly Pro Val Ala Ser Tyr Ala Ala Asp Ala Gly Tyr Thr Pro
            20                  25                  30

Ala Ala Ala Ala Thr Pro Ala Thr Ala Gly Gly Lys Ala Met Thr Glu
        35                  40                  45

Glu Gln Thr Leu Ile Glu Asp Val Asn Ala Gly Phe Lys Ala Ala Val
    50                  55                  60

Ala Ala Ala Ser Ser Ala Pro Pro Ala Asp Lys Phe Lys Thr Phe Glu
65                  70                  75                  80

Ala Thr Phe Thr Ala Ala Cys Lys Ala Asn Ile Ala Ala Ala Ala Thr
                85                  90                  95

Lys Val Pro Leu Phe Val Ala Lys Leu Asp Ala Ala Tyr Ala Val Ala
            100                 105                 110

Tyr Lys Thr Ala Thr Gly Pro Thr Pro Glu Ala Lys Tyr Asp Ala Phe
        115                 120                 125

Val Ala Ala Leu Thr Glu Ala Leu Arg Val Ile Ala Gly Ala Leu Glu
    130                 135                 140

Val His Ala Val Lys Pro Ala Ala Glu Glu Val Pro Ala Ala Lys Ile
145                 150                 155                 160

Pro Ala Gly Glu Leu Gln Ile Val Asp Lys Ile Asp Ala Ala Tyr Lys
                165                 170                 175

Ile Ala Ala Thr Ala Ala Asn Ala Ala Pro Ala Asn Asp Lys Phe Thr
            180                 185                 190

Val Phe Glu Gly Ala Phe Asn Lys Ala Ile Lys Glu Ser Thr Gly Gly
        195                 200                 205

Ala Tyr Glu Ser Tyr Lys Phe Ile Pro Thr Leu Glu Ala Ala Val Lys
    210                 215                 220
```

```
Gln Ala Tyr Ala Ala Thr Val Ala Ala Pro Glu Val Lys Tyr Ala
225                 230                 235                 240

Val Phe Glu Ala Ala Leu Thr Lys Ala Ile Thr Ala Met Ser Glu Ala
                245                 250                 255

Gln Lys Val Ala Thr Pro Ala Ala Val Ala Thr Gly Ala Ala Thr Ala
            260                 265                 270

Ala Ala Ser Ala Ala Thr Gly Ala Ala Thr Ala Ala Gly Gly Tyr
            275                 280                 285

Lys Val
    290

<210> SEQ ID NO 3
<211> LENGTH: 798
<212> TYPE: DNA
<213> ORGANISM: Dactylis glomerata
<220> FEATURE:
<221> NAME/KEY: CDS
<222> LOCATION: (1)..(795)
<223> OTHER INFORMATION: Dac g5 mature sequence

<400> SEQUENCE: 3 gcc gac gcc ggc tac acc ccg gcc gcc gcg gcc acc ccg gct acc gct      48
Ala Asp Ala Gly Tyr Thr Pro Ala Ala Ala Thr Pro Ala Thr Ala
1               5                   10                  15 gga ggg aag gcg atg acc gag gag cag acg cta atc gag gac gtc aat      96
Gly Gly Lys Ala Met Thr Glu Glu Gln Thr Leu Ile Glu Asp Val Asn
            20                  25                  30 gct ggt ttc aag gcg gcc gtg gcc gcc gcc tcc agt gcc cct ccg gcg     144
Ala Gly Phe Lys Ala Ala Val Ala Ala Ala Ser Ser Ala Pro Pro Ala
        35                  40                  45 gac aag ttc aag acc ttc gag gcc acc ttc act gcg gcc tgc aag gct     192
Asp Lys Phe Lys Thr Phe Glu Ala Thr Phe Thr Ala Ala Cys Lys Ala
    50                  55                  60 aac atc gcc gcc gcc gcc acc aag gtg ccc ctg ttc gtc gcc aag ctc     240
Asn Ile Ala Ala Ala Ala Thr Lys Val Pro Leu Phe Val Ala Lys Leu
65                  70                  75                  80 gac gcc gcc tac gcc gtc gcc tac aag acc gcc acg ggc ccc acc ccc     288
Asp Ala Ala Tyr Ala Val Ala Tyr Lys Thr Ala Thr Gly Pro Thr Pro
                85                  90                  95 gag gcc aag tac gac gcc ttc gtc gcc gcc ctc acc gaa gcg ctc cgc     336
Glu Ala Lys Tyr Asp Ala Phe Val Ala Ala Leu Thr Glu Ala Leu Arg
            100                 105                 110 gtt atc gcc ggc gcc ctc gaa gtc cat gcc gtc aag ccc gct gcc gag     384
Val Ile Ala Gly Ala Leu Glu Val His Ala Val Lys Pro Ala Ala Glu
        115                 120                 125 gag gtt ccc gcg gcc aag atc ccc gcc ggt gag ctg cag att gtc gac     432
Glu Val Pro Ala Ala Lys Ile Pro Ala Gly Glu Leu Gln Ile Val Asp
    130                 135                 140 aag atc gac gcc gcc tac aag atc gca gcc acc gct gca aac gcc gcc     480
Lys Ile Asp Ala Ala Tyr Lys Ile Ala Ala Thr Ala Ala Asn Ala Ala
145                 150                 155                 160 ccc gcc aac gac aag ttc acc gtc ttc gag ggc gcc ttc aac aag gcc     528
Pro Ala Asn Asp Lys Phe Thr Val Phe Glu Gly Ala Phe Asn Lys Ala
                165                 170                 175 atc aag gag agc acc ggc ggc gca tac gag agt tac aag ttc atc ccc     576
Ile Lys Glu Ser Thr Gly Gly Ala Tyr Glu Ser Tyr Lys Phe Ile Pro
            180                 185                 190 acg ctt gag gcc gcg gtc aag cag gct tac gcc gcc acc gtg gcc gcc     624
Thr Leu Glu Ala Ala Val Lys Gln Ala Tyr Ala Ala Thr Val Ala Ala
        195                 200                 205
```

```
gcg ccg gag gtc aag tac gcc gtc ttt gag gcc gcg ctg acc aag gcc      672
Ala Pro Glu Val Lys Tyr Ala Val Phe Glu Ala Ala Leu Thr Lys Ala
    210                 215                 220 atc acc gcc atg tcc gag gca cag aag gtc gcc acg cct gcc gcc gtt      720
Ile Thr Ala Met Ser Glu Ala Gln Lys Val Ala Thr Pro Ala Ala Val
225                 230                 235                 240 gct aca ggt gcg gca acc gcc gct gcc agt gct gct acc ggc gct gcc      768
Ala Thr Gly Ala Ala Thr Ala Ala Ala Ser Ala Ala Thr Gly Ala Ala
                245                 250                 255 acc gcc gct gcc ggt ggc tac aaa gtc tga                              798
Thr Ala Ala Ala Gly Gly Tyr Lys Val
            260                 265

<210> SEQ ID NO 4
<211> LENGTH: 265
<212> TYPE: PRT
<213> ORGANISM: Dactylis glomerata

<400> SEQUENCE: 4

Ala Asp Ala Gly Tyr Thr Pro Ala Ala Ala Thr Pro Ala Thr Ala
1               5                   10                  15

Gly Gly Lys Ala Met Thr Glu Glu Gln Thr Leu Ile Glu Asp Val Asn
            20                  25                  30

Ala Gly Phe Lys Ala Ala Val Ala Ala Ser Ser Ala Pro Pro Ala
        35                  40                  45

Asp Lys Phe Lys Thr Phe Glu Ala Thr Phe Thr Ala Ala Cys Lys Ala
    50                  55                  60

Asn Ile Ala Ala Ala Thr Lys Val Pro Leu Phe Val Ala Lys Leu
65                  70                  75                  80

Asp Ala Ala Tyr Ala Val Ala Tyr Lys Thr Ala Thr Gly Pro Thr Pro
                85                  90                  95

Glu Ala Lys Tyr Asp Ala Phe Val Ala Ala Leu Thr Glu Ala Leu Arg
            100                 105                 110

Val Ile Ala Gly Ala Leu Glu Val His Ala Val Lys Pro Ala Ala Glu
        115                 120                 125

Glu Val Pro Ala Ala Lys Ile Pro Ala Gly Glu Leu Gln Ile Val Asp
    130                 135                 140

Lys Ile Asp Ala Ala Tyr Lys Ile Ala Ala Thr Ala Ala Asn Ala Ala
145                 150                 155                 160

Pro Ala Asn Asp Lys Phe Thr Val Phe Glu Gly Ala Phe Asn Lys Ala
                165                 170                 175

Ile Lys Glu Ser Thr Gly Gly Ala Tyr Glu Ser Tyr Lys Phe Ile Pro
            180                 185                 190

Thr Leu Glu Ala Ala Val Lys Gln Ala Tyr Ala Ala Thr Val Ala Ala
        195                 200                 205

Ala Pro Glu Val Lys Tyr Ala Val Phe Glu Ala Ala Leu Thr Lys Ala
    210                 215                 220

Ile Thr Ala Met Ser Glu Ala Gln Lys Val Ala Thr Pro Ala Ala Val
225                 230                 235                 240

Ala Thr Gly Ala Ala Thr Ala Ala Ala Ser Ala Ala Thr Gly Ala Ala
                245                 250                 255

Thr Ala Ala Ala Gly Gly Tyr Lys Val
            260                 265

<210> SEQ ID NO 5
<211> LENGTH: 798
```

```
<212> TYPE: DNA
<213> ORGANISM: Dactylis glomerata
<220> FEATURE:
<221> NAME/KEY: CDS
<222> LOCATION: (1)..(795)
<223> OTHER INFORMATION: Dac g5 mature sequence isoform 1

<400> SEQUENCE: 5 gcc gac gcc ggc tac acc ccg gcc gcc gcg gcc acc ccg gct acc gct      48
Ala Asp Ala Gly Tyr Thr Pro Ala Ala Ala Ala Thr Pro Ala Thr Ala
 1               5                  10                  15 gga ggg aag gcg atg acc gag gag cag acg cta atc gag gac gtc aat      96
Gly Gly Lys Ala Met Thr Glu Glu Gln Thr Leu Ile Glu Asp Val Asn
             20                  25                  30 gct ggt ttc aag gcg gcc gtg gcc gcc gcc tcc agt gcc cct ccg gcg     144
Ala Gly Phe Lys Ala Ala Val Ala Ala Ala Ser Ser Ala Pro Pro Ala
         35                  40                  45 gac aag ttc aag acc ttc gag gcc acc ttc acc gcg gcc tgc aag gct     192
Asp Lys Phe Lys Thr Phe Glu Ala Thr Phe Thr Ala Ala Cys Lys Ala
     50                  55                  60 aac atc gcc gcc gcc gcc acc aag gtg ccc ctg ttc gtc gcc aag ctc     240
Asn Ile Ala Ala Ala Ala Thr Lys Val Pro Leu Phe Val Ala Lys Leu
 65                  70                  75                  80 gac gcc gcc tac gcc gtc gcc tac aag acc gcc acg ggc ccc acc ccc     288
Asp Ala Ala Tyr Ala Val Ala Tyr Lys Thr Ala Thr Gly Pro Thr Pro
                 85                  90                  95 gag gcc aag tac gac gcc ttc gtc gcc gcc ctc acc gaa gcg ctc cgc     336
Glu Ala Lys Tyr Asp Ala Phe Val Ala Ala Leu Thr Glu Ala Leu Arg
            100                 105                 110 gtt atc gcc ggc gcc ctc gaa gtc cac gcc gtc aag ccc gct gcc gag     384
Val Ile Ala Gly Ala Leu Glu Val His Ala Val Lys Pro Ala Ala Glu
        115                 120                 125 gag gtt ccc gcg gcc aag atc ccc gcc ggt gag ctg cag att gtc gac     432
Glu Val Pro Ala Ala Lys Ile Pro Ala Gly Glu Leu Gln Ile Val Asp
    130                 135                 140 aag atc gac gcc gcc tac aag atc gca gcc acc gcc gca aac gcc gcc     480
Lys Ile Asp Ala Ala Tyr Lys Ile Ala Ala Thr Ala Ala Asn Ala Ala
145                 150                 155                 160 ccc gcc aac gac aag ttc acc gtc ttc gag ggc gcc ttc aac aag gcc     528
Pro Ala Asn Asp Lys Phe Thr Val Phe Glu Gly Ala Phe Asn Lys Ala
                165                 170                 175 atc aag gag agc acc ggc ggc gca tac gag agt tac aag ttc atc ccc     576
Ile Lys Glu Ser Thr Gly Gly Ala Tyr Glu Ser Tyr Lys Phe Ile Pro
            180                 185                 190 acg ctt gag gcc gcg gtc aag cag gcc tac gcc gcc acc gtg gcc gcc     624
Thr Leu Glu Ala Ala Val Lys Gln Ala Tyr Ala Ala Thr Val Ala Ala
        195                 200                 205 gcg ccc gag gtc aag tac gcc gtc ttt gag gcc gcg ctg acc aag gcc     672
Ala Pro Glu Val Lys Tyr Ala Val Phe Glu Ala Ala Leu Thr Lys Ala
    210                 215                 220 atc acc gcc atg tcc gag gca cag aag gtc gcc acg cct gcc gcc gtt     720
Ile Thr Ala Met Ser Glu Ala Gln Lys Val Ala Thr Pro Ala Ala Val
225                 230                 235                 240 gct aca ggt gcg gca acc gcc gct gcc agt gct gct acc ggc gct gcc     768
Ala Thr Gly Ala Ala Thr Ala Ala Ala Ser Ala Ala Thr Gly Ala Ala
                245                 250                 255 acc gcc gct gcc ggt ggc tac aaa gtc tga                             798
Thr Ala Ala Ala Gly Gly Tyr Lys Val
            260                 265

<210> SEQ ID NO 6
```

<211> LENGTH: 265
<212> TYPE: PRT
<213> ORGANISM: Dactylis glomerata

<400> SEQUENCE: 6

```
Ala Asp Ala Gly Tyr Thr Pro Ala Ala Ala Thr Pro Ala Thr Ala
  1               5                  10                  15

Gly Gly Lys Ala Met Thr Glu Glu Gln Thr Leu Ile Glu Asp Val Asn
             20                  25                  30

Ala Gly Phe Lys Ala Ala Val Ala Ala Ser Ser Ala Pro Pro Ala
         35                  40                  45

Asp Lys Phe Lys Thr Phe Glu Ala Thr Phe Thr Ala Ala Cys Lys Ala
 50                  55                  60

Asn Ile Ala Ala Ala Thr Lys Val Pro Leu Phe Val Ala Lys Leu
 65                  70                  75                  80

Asp Ala Ala Tyr Ala Val Ala Tyr Lys Thr Ala Thr Gly Pro Thr Pro
                 85                  90                  95

Glu Ala Lys Tyr Asp Ala Phe Val Ala Ala Leu Thr Glu Ala Leu Arg
            100                 105                 110

Val Ile Ala Gly Ala Leu Glu Val His Ala Val Lys Pro Ala Ala Glu
            115                 120                 125

Glu Val Pro Ala Ala Lys Ile Pro Ala Gly Glu Leu Gln Ile Val Asp
130                 135                 140

Lys Ile Asp Ala Ala Tyr Lys Ile Ala Ala Thr Ala Ala Asn Ala Ala
145                 150                 155                 160

Pro Ala Asn Asp Lys Phe Thr Val Phe Glu Gly Ala Phe Asn Lys Ala
                165                 170                 175

Ile Lys Glu Ser Thr Gly Gly Ala Tyr Glu Ser Tyr Lys Phe Ile Pro
            180                 185                 190

Thr Leu Glu Ala Ala Val Lys Gln Ala Tyr Ala Ala Thr Val Ala Ala
            195                 200                 205

Ala Pro Glu Val Lys Tyr Ala Val Phe Glu Ala Ala Leu Thr Lys Ala
210                 215                 220

Ile Thr Ala Met Ser Glu Ala Gln Lys Val Ala Thr Pro Ala Ala Val
225                 230                 235                 240

Ala Thr Gly Ala Ala Thr Ala Ala Ala Ser Ala Ala Thr Gly Ala Ala
                245                 250                 255

Thr Ala Ala Ala Gly Gly Tyr Lys Val
            260                 265
```

<210> SEQ ID NO 7
<211> LENGTH: 798
<212> TYPE: DNA
<213> ORGANISM: Dactylis glomerata
<220> FEATURE:
<221> NAME/KEY: CDS
<222> LOCATION: (1)..(795)
<223> OTHER INFORMATION: Dac g5 mature sequence isoform 2

<400> SEQUENCE: 7

```
gcc gac gcc ggc tac acc ccg gcc gcc gcg gcc acc ccg gct gct gct     48
Ala Asp Ala Gly Tyr Thr Pro Ala Ala Ala Thr Pro Ala Ala Ala
  1               5                  10                  15 gga ggg aag gcg atg acc gag gag cag aag cta atc gag gac gtc aac     96
Gly Gly Lys Ala Met Thr Glu Glu Gln Lys Leu Ile Glu Asp Val Asn
             20                  25                  30 gct ggc ttc aag gcg gcc gtg gcc gcc gcc tcc agt gcc cct ccg gcg    144
Ala Gly Phe Lys Ala Ala Val Ala Ala Ala Ser Ser Ala Pro Pro Ala
```

```
                35                  40                  45
gac aag ttc aag acc ttc gag gcc acc ttc acc gcg gcc tgc aag gct       192
Asp Lys Phe Lys Thr Phe Glu Ala Thr Phe Thr Ala Ala Cys Lys Ala
 50                  55                  60 aac atc gcc gcc gcc gcc acc aag gtg ccc ctg ttc gtc gcc aag ctc       240
Asn Ile Ala Ala Ala Ala Thr Lys Val Pro Leu Phe Val Ala Lys Leu
 65                  70                  75                  80 gac gcc gcc tac gcc gtc gcc tac aag acc gcc gcg ggc ccc acc ccc       288
Asp Ala Ala Tyr Ala Val Ala Tyr Lys Thr Ala Ala Gly Pro Thr Pro
                 85                  90                  95 gag gcc aag tac gac gcc ttt gtc gcc gcc ctc acc gaa gca ctc cgc       336
Glu Ala Lys Tyr Asp Ala Phe Val Ala Ala Leu Thr Glu Ala Leu Arg
            100                 105                 110 gtt atc gcc ggc gcc ctc gaa gtc cac gcc gtc aag ccc gct gcc gag       384
Val Ile Ala Gly Ala Leu Glu Val His Ala Val Lys Pro Ala Ala Glu
        115                 120                 125 gag gtt ccc gcg gcc aag atc ccc gcc ggt gag ctg cag att gtc gac       432
Glu Val Pro Ala Ala Lys Ile Pro Ala Gly Glu Leu Gln Ile Val Asp
    130                 135                 140 aag atc gac gcc gcc tac aag atc gca gcc acc gcc gca aac gcc gcc       480
Lys Ile Asp Ala Ala Tyr Lys Ile Ala Ala Thr Ala Ala Asn Ala Ala
145                 150                 155                 160 ccc gcc aac gac aag ttc acc gtc ttc gag ggc gcc ttc aac aag gcc       528
Pro Ala Asn Asp Lys Phe Thr Val Phe Glu Gly Ala Phe Asn Lys Ala
                165                 170                 175 atc aag gag agc acc ggc ggc gca tac gag agt tac aag ttc atc ccc       576
Ile Lys Glu Ser Thr Gly Gly Ala Tyr Glu Ser Tyr Lys Phe Ile Pro
            180                 185                 190 acg ctt gag gcc gcg gtc aag cag gcc tac gcc gcc acc gtg gcc gcc       624
Thr Leu Glu Ala Ala Val Lys Gln Ala Tyr Ala Ala Thr Val Ala Ala
        195                 200                 205 gcg ccc gag gtc aag tac gcc gtc ttt gag gcc gcg ctg acc aag gcc       672
Ala Pro Glu Val Lys Tyr Ala Val Phe Glu Ala Ala Leu Thr Lys Ala
    210                 215                 220 atc acc gcc atg tcc gag gca cag aag gtc gcc acg ccc gcc gcc gct       720
Ile Thr Ala Met Ser Glu Ala Gln Lys Val Ala Thr Pro Ala Ala Ala
225                 230                 235                 240 gct aca ggt gcg gca acc gcc gct gcc agt gct gct acc ggc gct gcc       768
Ala Thr Gly Ala Ala Thr Ala Ala Ala Ser Ala Ala Thr Gly Ala Ala
                245                 250                 255 acc gcc gct gcc ggt ggc tac aaa gtc tga                                798
Thr Ala Ala Ala Gly Gly Tyr Lys Val
            260                 265

<210> SEQ ID NO 8
<211> LENGTH: 265
<212> TYPE: PRT
<213> ORGANISM: Dactylis glomerata

<400> SEQUENCE: 8

Ala Asp Ala Gly Tyr Thr Pro Ala Ala Ala Thr Pro Ala Ala Ala
 1               5                  10                  15

Gly Gly Lys Ala Met Thr Glu Glu Gln Lys Leu Ile Glu Asp Val Asn
                20                  25                  30

Ala Gly Phe Lys Ala Ala Val Ala Ala Ser Ser Ala Pro Pro Ala
            35                  40                  45

Asp Lys Phe Lys Thr Phe Glu Ala Thr Phe Thr Ala Ala Cys Lys Ala
 50                  55                  60

Asn Ile Ala Ala Ala Ala Thr Lys Val Pro Leu Phe Val Ala Lys Leu
```

```
                65                  70                  75                  80
Asp Ala Ala Tyr Ala Val Ala Tyr Lys Thr Ala Gly Pro Thr Pro
                    85                  90                  95

Glu Ala Lys Tyr Asp Ala Phe Val Ala Leu Thr Glu Ala Leu Arg
                100                 105                 110

Val Ile Ala Gly Ala Leu Glu Val His Ala Val Lys Pro Ala Ala Glu
            115                 120                 125

Glu Val Pro Ala Ala Lys Ile Pro Ala Gly Glu Leu Gln Ile Val Asp
        130                 135                 140

Lys Ile Asp Ala Ala Tyr Lys Ile Ala Ala Thr Ala Ala Asn Ala Ala
145                 150                 155                 160

Pro Ala Asn Asp Lys Phe Thr Val Phe Glu Gly Ala Phe Asn Lys Ala
                165                 170                 175

Ile Lys Glu Ser Thr Gly Gly Ala Tyr Glu Ser Tyr Lys Phe Ile Pro
                180                 185                 190

Thr Leu Glu Ala Ala Val Lys Gln Ala Tyr Ala Ala Thr Val Ala Ala
            195                 200                 205

Ala Pro Glu Val Lys Tyr Ala Val Phe Glu Ala Ala Leu Thr Lys Ala
        210                 215                 220

Ile Thr Ala Met Ser Glu Ala Gln Lys Val Ala Thr Pro Ala Ala Ala
225                 230                 235                 240

Ala Thr Gly Ala Ala Thr Ala Ala Ser Ala Ala Thr Gly Ala Ala
                245                 250                 255

Thr Ala Ala Gly Gly Tyr Lys Val
            260                 265
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
gggtctagaa tggcggtcca gaagtacacc                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
ggggagctct cagactttgt agccaccggc                                    30

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 11
aagctcgaga aaagagccga cgccggctac acc                                33

<210> SEQ ID NO 12
<211> LENGTH: 33
<212> TYPE: DNA
<213> ORGANISM: Artificial Sequence -continued

```
<220> FEATURE:
<223> OTHER INFORMATION: Description of Artificial Sequence: Primer

<400> SEQUENCE: 12
gggggcggcc gctcagactt tgtagccacc ggc                                    33
```